(12) United States Patent
Loccufier et al.

(10) Patent No.: US 7,090,902 B2
(45) Date of Patent: Aug. 15, 2006

(54) INK JET RECORDING MATERIAL

(75) Inventors: Johan Loccufier, Zwijnaarde (BE); Stefaan Lingier, Assenede (BE)

(73) Assignee: AGFA-GEVAERT, Mortsel (BE)

( * ) Notice: Subject to any disclaimer, the term of this patent is extended or adjusted under 35 U.S.C. 154(b) by 68 days.

(21) Appl. No.: 10/657,466

(22) Filed: Sep. 8, 2003

(65) Prior Publication Data

US 2004/0052981 A1    Mar. 18, 2004

Related U.S. Application Data

(60) Provisional application No. 60/412,837, filed on Sep. 23, 2002.

(30) Foreign Application Priority Data

Sep. 11, 2002    (EP) ............... 02102340

(51) Int. Cl.
*B41M 5/00*    (2006.01)
(52) U.S. Cl. .................... 428/32.1
(58) Field of Classification Search ............ None
See application file for complete search history.

(56) References Cited

U.S. PATENT DOCUMENTS 5,338,853 A * 8/1994 MacLeay et al. ........ 546/224
2003/0175451 A1* 9/2003 Wickramanayake et al. .... 428/32.36

FOREIGN PATENT DOCUMENTS

JP    61-146591    7/1986
WO    01/20078    3/2001

OTHER PUBLICATIONS

European Search Report, EP02102340; published Mar. 3, 2003; Author—Markham, R.
Japanese Patent Abstracts XP-002225590, published Jul. 4, 1986, Mitsubishi Paper Mills LTD.

* cited by examiner

*Primary Examiner*—Pamela R. Schwartz
(74) *Attorney, Agent, or Firm*—Joseph T. Guy; Nexsen Pruet, LLC

(57) ABSTRACT

An ink jet recording material is disclosed comprising a support and at least one binder containing ink-receiving layer, further containing a light-stabilizing compound according to following general formula (I):

$$A\text{-}L\text{-}R \quad (I)$$

wherein,

A is represented by following formula:

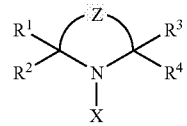

the symbols of which are defined in the claims and description. The finished ink jet image shows an improved light-fastness.

7 Claims, No Drawings

INK JET RECORDING MATERIAL

CROSS-REFERENCE TO RELATED PATENT APPLICATIONS

This application claims the benefit of U.S. Provisional Application No. 60/412,837 filed Sep. 23, 2002, which is incorporated by reference. In addition, this application claims the benefit of European Application No. 02102340.3 filed Sep. 11, 2002, which is also incorporated by reference.

FIELD OF THE INVENTION

The present invention relates to an ink jet recording material having an improved stabilization of the finished image against color fading due to light.

BACKGROUND OF THE INVENTION

In the majority of applications printing proceeds by pressure contact of an ink-laden printing form with an ink-receiving material which is usually plain paper. The most frequently used impact printing technique is known as lithographic printing based on the selective acceptance of oleophilic ink on a suitable receptor.

In recent times however so-called non-impact printing systems have replaced classical pressure-contact printing to some extent for specific applications. A survey is given e.g. in the book "Principles of Non Impact Printing" by Jerome L. Johnson (1986), Palatino Press, Irvine, Calif. 92715, USA.

Among non-impact printing techniques ink jet printing has become a popular technique because of its simplicity, convenience and low cost. Especially in those instances where a limited edition of the printed matter is needed ink jet printing has become a technology of choice. A recent survey on progress and trends in ink jet printing technology is given by Hue P. Le in *Journal of Imaging Science and Technology* Vol. 42 (1), January/February 1998.

In ink jet printing tiny drops of ink fluid are projected directly onto an ink receptor surface without physical contact between the printing device and the receptor. The printing device stores the printing data electronically and controls a mechanism for ejecting the drops image-wise. Printing is accomplished by moving the print head across the paper or vice versa. Early patents on ink jet printers include U.S. Pat. No. 3,739,393, U.S. Pat. No. 3,805,273 and U.S. Pat. No. 3,891,121.

The jetting of the ink droplets can be performed in several different ways. In a first type of process a continuous droplet stream is created by applying a pressure wave pattern. This process is known as continuous ink jet printing. In a first embodiment the droplet stream is divided into droplets that are electrostatically charged, deflected and recollected, and into droplets that remain uncharged, continue their way undeflected, and form the image. Alternatively, the charged deflected stream forms the image and the uncharged undeflected jet is recollected. In this variant of continuous ink jet printing several jets are deflected to a different degree and thus record the image (multideflection system).

According to a second process the ink droplets can be created "on demand" ("DOD" or "drop on demand" method) whereby the printing device ejects the droplets only when they are used in imaging on a receiver thereby avoiding the complexity of drop charging, deflection hardware, and ink recollection. In drop-on-demand the ink droplet can be formed by means of a pressure wave created by a mechanical motion of a piezoelectric transducer (so-called "piezo method"), or by means of discrete thermal pushes (so-called "bubble jet" method, or "thermal jet" method).

Ink compositions for ink jet typically include following ingredients: dyes or pigments, water and/or organic solvents, humectants such as glycols, detergents, thickeners, polymeric binders, preservatives, etc. It will be readily understood that the optimal composition of such an ink is dependent on the ink jetting method used and on the nature of the substrate to be printed. The ink compositions can be roughly divided in:

water based; the drying mechanism involves absorption, penetration and evaporation;

oil based; the drying involves absorption and penetration;

solvent based; the drying mechanism involves primarely evaporation;

hot melt or phase change: the ink vehicle is liquid at the ejection temperature but solid at room temperature; drying is replaced by solidification;

UV-curable; drying is replaced by polymerization.

WO 01/020078 discloses a compound of any of formulas I to X, or IA to XA

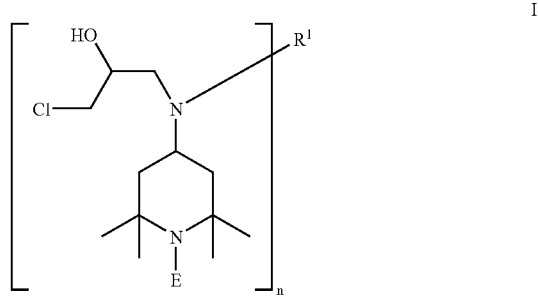

I

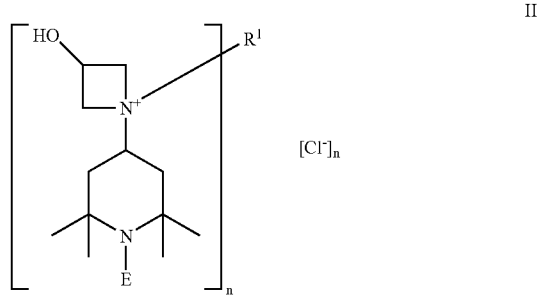

II

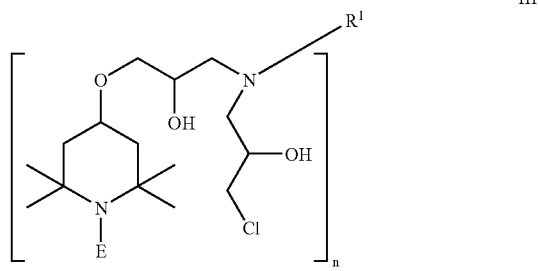

III

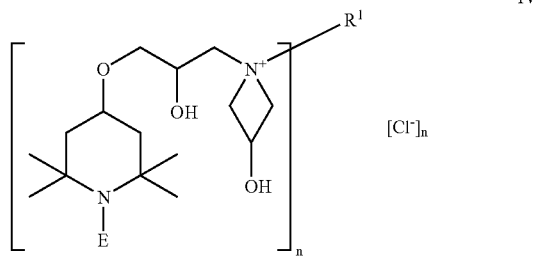

IV

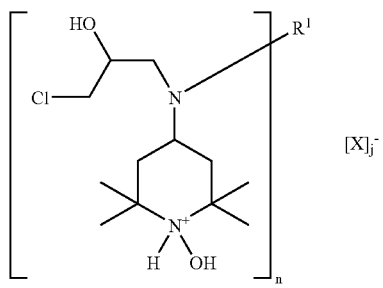
IA
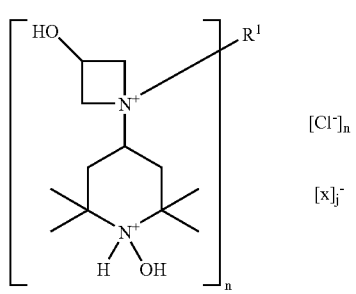
IIA
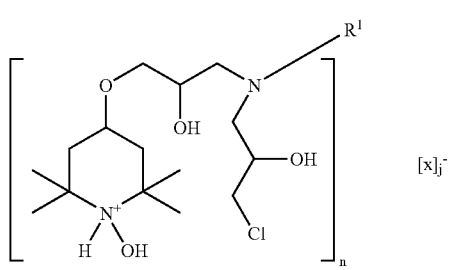
IIIA
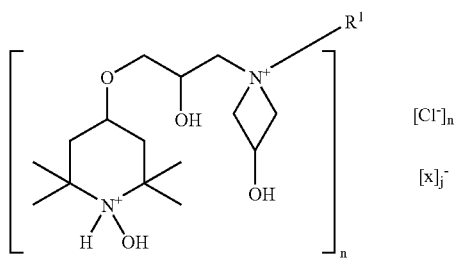
IVA
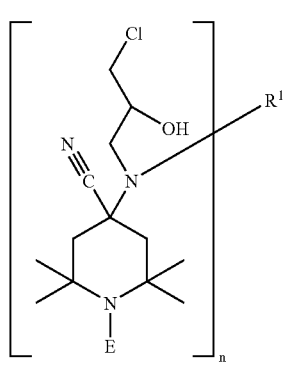
V
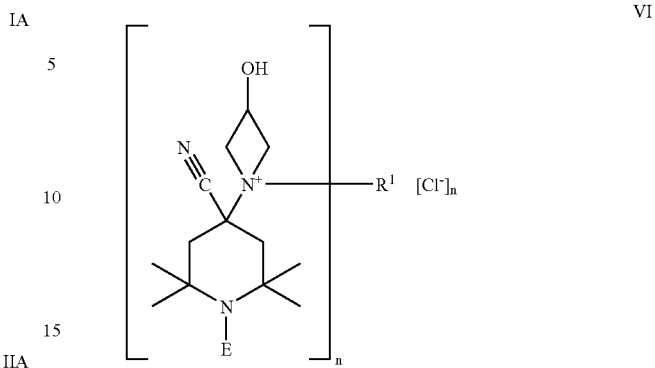
VI
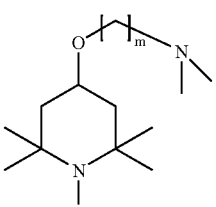
VII
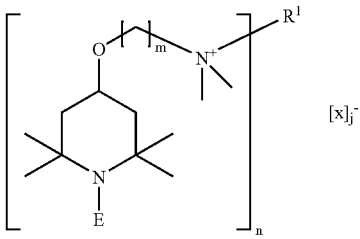
VIII
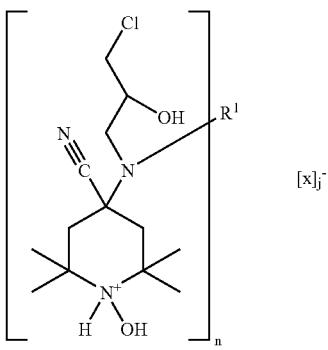
VA
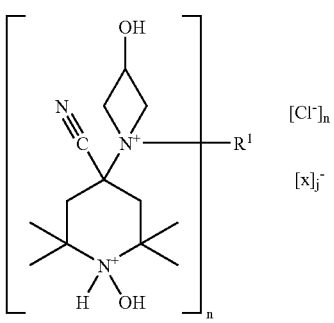
VIA -continued
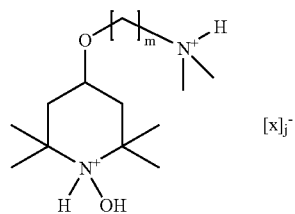
VIIA
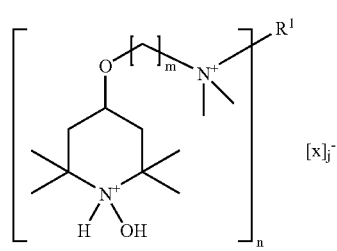
VIIIA
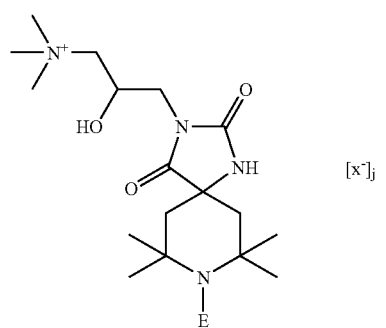
IX
-continued
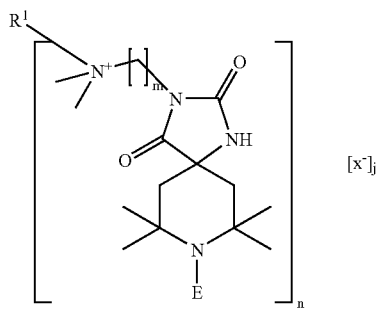
X
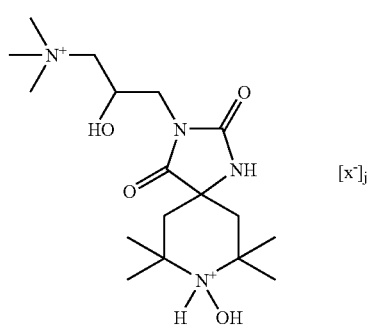
IXA
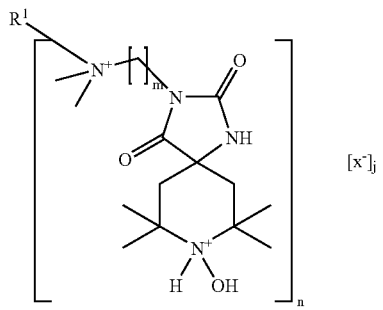
XA
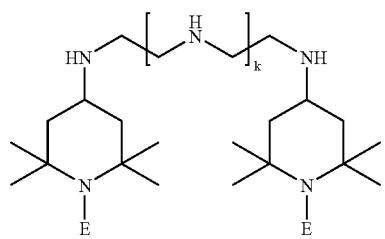
+ 1 to k + 2 equiv.
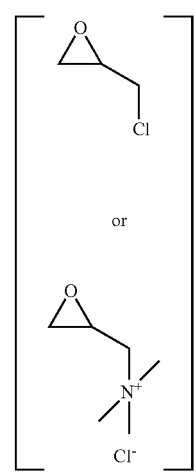
XI -continued
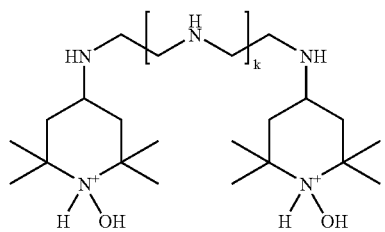
[X]$_j^-$
+ 1 to k + 2 equiv.
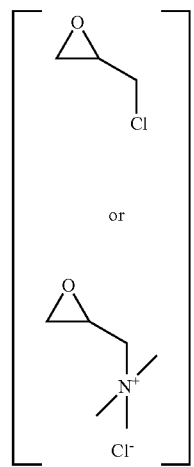
XIA
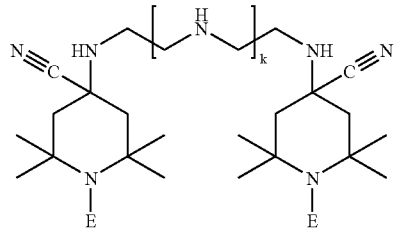
+ 1 to k + 2 equiv.
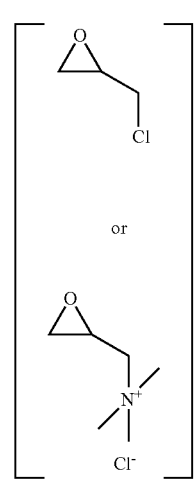
XII
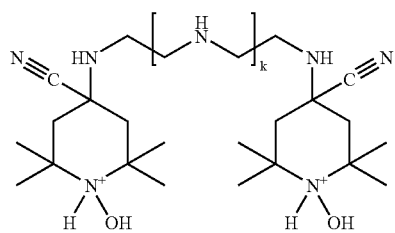
[X]$_j^-$
+ 1 to k + 2 equiv.
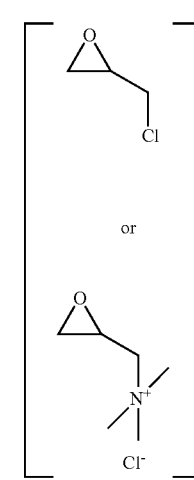
XIIA XIII
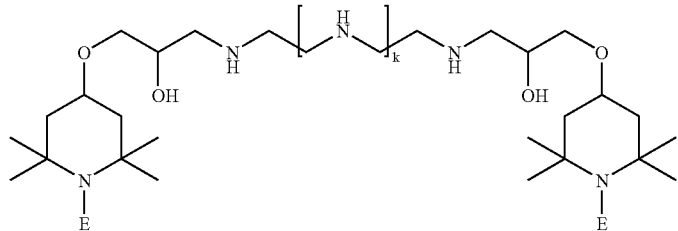
+
1 to k + 2 equiv. 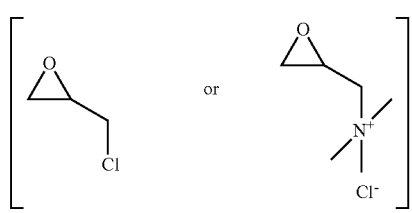
XIIIA
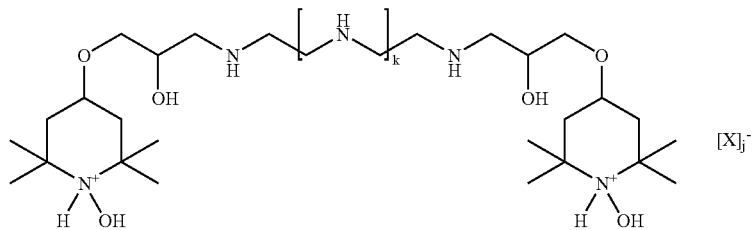 [X]$_j^-$
+
1 to k + 2 equiv. 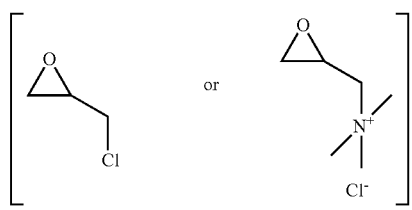
XIV
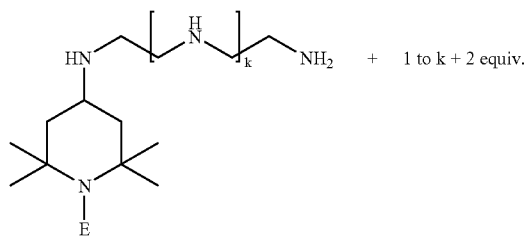 + 1 to k + 2 equiv. 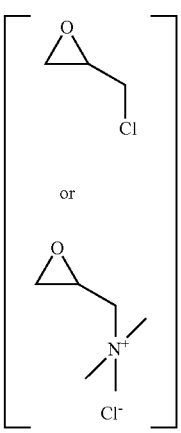

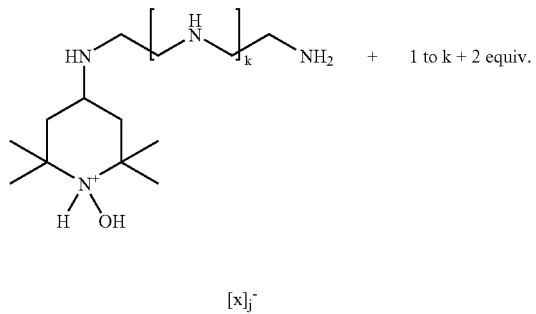 + 1 to k + 2 equiv. 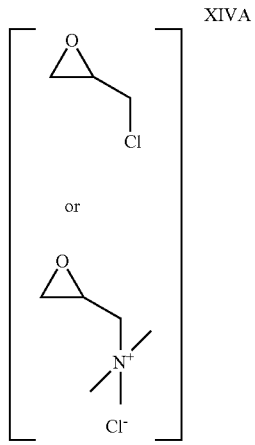
XIVA
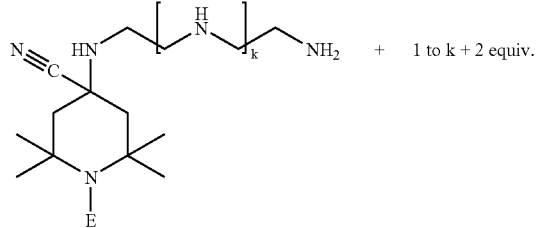 + 1 to k + 2 equiv. 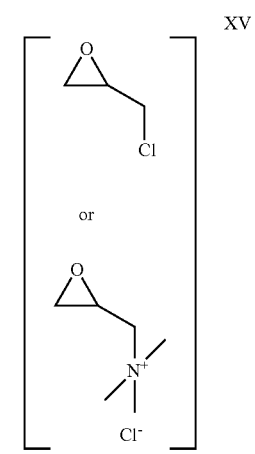
XV
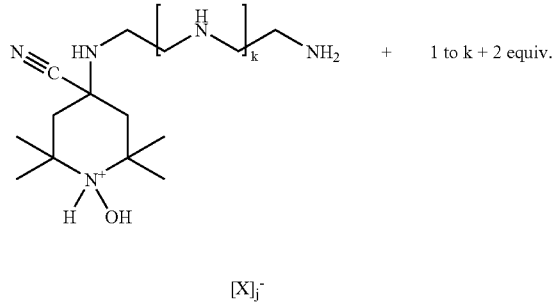 + 1 to k + 2 equiv. 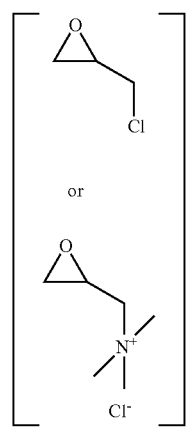
XVA

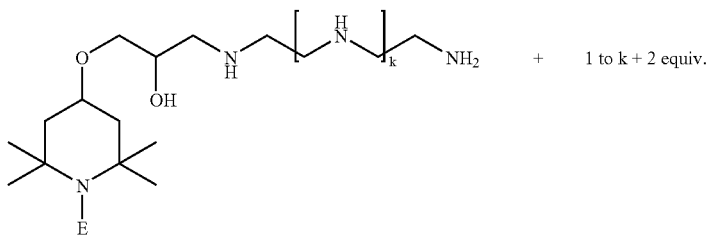 + 1 to k + 2 equiv. 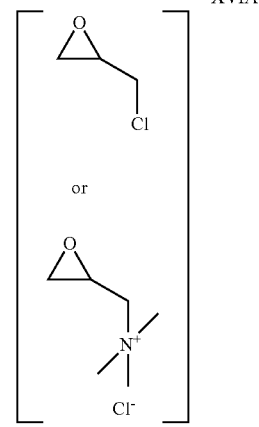

XVI

XVIA

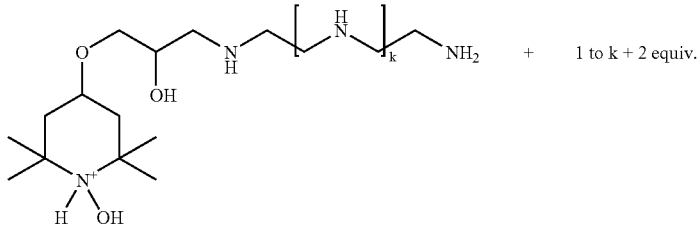 + 1 to k + 2 equiv.

[X]⁻ⱼ

U.S. Pat. No. 6,232,469 discloses 4-acylamino-2,2,6,6-tetramethyl-piperidine derivatives represented by formula (A'):

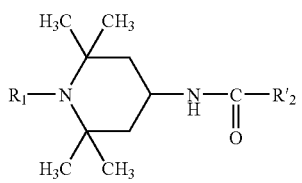

wherein $R_1$ represents a hydrogen atom, a hydroxyl group, an oxyradical group, an aliphatic group, an acyl group, an aliphatic oxy group or an acyloxy group; and $R_2'$ represents an alkyl group or an alkenyl group having 3 to 7 carbon atoms and 2 to 6 hydroxyl groups, said alkyl or alkenyl group being unsubstituted or substituted with an alkyl group. U.S. Pat. No. 6,232,469 further discloses an antioxidant composition for color diffusion transfer photographic materials or ink-jet dyes comprising the 4-acylamino-2,2,6,6-tetramethylpiperidine derivatives represented by formula (A):

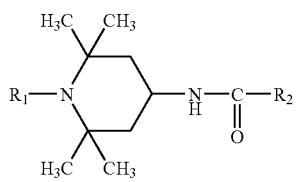

wherein $R_1$ represents a hydrogen atom, a hydroxyl group, an oxyradical group, an aliphatic group, an acyl group, an aliphatic oxy group or an acyloxy group; and $R_2$ represents an alkyl group or an alkenyl group having 3 to 7 carbon atoms and 2 to 6 hydroxyl groups.

JP 61-146591 discloses an ink-jet recording medium that form a recording image using aqueous ink that contains a water-soluble dye, characterized in that the recording medium contains a hindered amine type compound, in particular a molecule represented by formula (I):

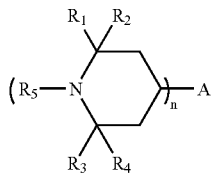

wherein R$_5$ is a hydrogen atom or an alkyl group of C$_1$ to C$_8$, a benzyl group, an allyl group or an acetyl group and preferably a hydrogen atom or a methyl group; R$_1$, R$_2$, R$_3$ and R$_4$ are lower alkyl groups, carbonyl groups etc. and preferably methyl groups and/or ethyl groups. JP 61-146591 further discloses that if n=1, A is —NH$_2$, —OH, =CH$_2$, =O, —R, —OR, —OCO—R, —NHCH$_2$CH$_2$CH$_2$OCH$_3$, —NHCSSH, phenyl, —CH=CH$_2$, (here R is an alkyl group),

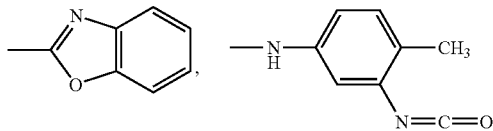

etc.; and if n=2 A is —O—C(=O)—(CH$_2$)$_m$—C(=O)—O— (m is 1 to 14),

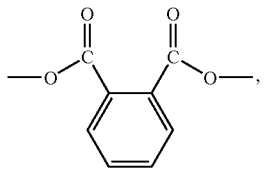

—NH(CH$_2$)$_3$NH—,

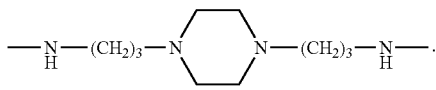

It is known that the ink-receiving layers in ink-jet recording elements must meet different stringent requirements:

the ink-receiving layer should have a high ink absorbing capacity, so that the dots will not flow out and will not be expanded more than is necessary to obtain a high optical density;

the ink-receiving layer should have a high ink absorbing speed (short ink drying time) so that the ink droplets will not feather if smeared immediately after applying;

the ink dots that are applied to the ink-receiving layer should be substantially round in shape and smooth at their peripheries. The dot diameter must be constant and accurately controlled;

the receiving layer must be readily wetted so that there is no "puddling", i.e. coalescence of adjacent ink dots, and an earlier absorbed ink drop should not show any "bleeding", i.e. overlap with neighbouring or later placed dots;

transparent ink-jet recording elements must have a low haze-value and be excellent in transmittance properties;

after being printed the image must have a good resistance regarding water-fastness, light-fastness, and good endurance under severe conditions of temperature and humidity;

the ink jet recording element may not show any curl or sticky behaviour if stacked before or after being printed;

the ink jet recording element must be able to move smoothly through different types of printers;

All these properties are often in a relation of trade-off. It is difficult to satisfy them all at the same time.

A particular problem is the stability of the color densities of the finished color ink jet image when exposed to light for a longer period ("light-fastness"). As well-known by those skilled in the art, the light fading of colorants is mainly due to an oxidative decomposition of the colorant catalyzed by light, in particular by the UV spectral part. Therefore, there is a permanent need of more effective compounds, which stabilize the colorants of the ink jet image against fading by light.

OBJECTS OF THE INVENTION

It is therefore an object of the present invention to provide an ink jet recording material with an improvement in light-fastness.

It is therefore a further object of the present invention to provide a compound having light-stabilizing properties.

Further objects and advantages of the present invention will become apparent from the description hereinafter.

SUMMARY OF THE INVENTION

It has been surprisingly found that when an ink jet recording material contains a compound represented by formula (I): A-L-R, wherein L is a divalent linking group, linked to the five- or six-membered ring by one of the atoms of Z, optionally by a double bond, characterized in that it comprises a nitrogen-nitrogen or nitrogen-oxygen bond; R represents a non aromatic moiety comprising at least two hydroxyl groups; and A is represented by following formula:

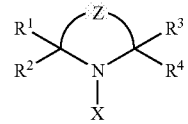

where Z represents the necessary atoms to complete a five- or six-membered ring, R$^1$ to R$^4$ independently represent a substituted or unsubstituted C1 to C6 aliphatic group, X is selected from the group consisting of a hydrogen, a substituted or unsubstituted aliphatic group, an acyl group, an oxy radical, a hydroxyl group, an alkoxy group, an —OSO$_2$-alkyl group, and an acyloxy group, exhibit a strong improvement in light-fastness.

Objects of the present invention are realized by providing an ink jet recording material comprising a support and at least one binder-containing ink-receiving layer, characterized in that said at least one ink-receiving layer further contains a light-stabilizing compound according to formula (I):

A-L-R       (I)

wherein A is represented by following formula:

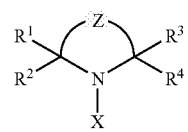

wherein Z represents the necessary atoms to complete a five- or six-membered ring, R$^1$ to R$^4$ independently represent a substituted or unsubstituted C1 to C6 aliphatic group, X is selected from the group consisting of a hydrogen, a substituted or unsubstituted aliphatic group, an acyl group, an oxy radical, a hydroxyl group, an alkoxy group, an —OSO$_2$-alkyl group, and an acyloxy group; L is a divalent linking group, linked to the five- or six-membered ring by one of the atoms of Z, optionally by a double bond, wherein said divalent linking group comprises a nitrogen-nitrogen or nitrogen-oxygen bond; and R represents a non aromatic moiety comprising at least two hydroxyl groups.

Objects of the present invention are also realized by providing a compound represented by following formula:

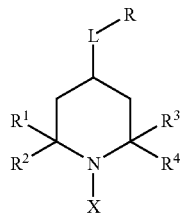

wherein $R^1$ to $R^4$ independently represent a substituted or unsubstituted C1 to C6 aliphatic group, X is selected from the group consisting of a hydrogen, a substituted or unsubstituted aliphatic group, an acyl group, an oxy radical, a hydroxyl group, an alkoxy group a —OSO$_2$-alkyl group, and an acyloxy group; L is a divalent linking group, linked to the six-membered ring optionally by a double bond, wherein said divalent linking group comprises a nitrogen-nitrogen or nitrogen-oxygen bond; and R represents a non-aromatic moiety comprising at least two hydroxyl groups.

Further advantages and embodiments of the present invention will become apparent from the following description.

DETAILED DESCRIPTION OF THE INVENTION

Definitions

The term divalent linking group as used in disclosing the present invention refers to a linkage group linking two entities by covalent bonds, regardless of whether the linkage group is linked to each of these entities via a single, double or triple bond.

The term alkyl means all variants possible for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethylpropyl, 2,2-dimethylpropyl and 2-methyl-butyl etc.

The term acyl group as used in disclosing the present invention means —(C=O)-aryl and —(C=O)-alkyl groups.

The term aliphatic group includes straight chain, branched chain and alicyclic hydrocarbon groups, which may contain at least one double or triple bond, but are not aromatic.

Ink-Recording Material

The different layers and particular ingredients of the ink-recording material, according to the present invention, will now be explained in detail.

Support

The support for use in the present invention can be chosen from paper type and polymeric type supports well-known from photographic technology. Paper types include plain paper, cast coated paper, polyethylene coated paper and polypropylene coated paper. Polymeric supports include cellulose acetate propionate or cellulose acetate butyrate, polyesters such as polyethylene terephthalate and polyethylene naphthalate, polyamides, polycarbonates, polyimides, polyolefins, poly(vinylacetals), polyethers and polysulfonamides. Other examples of useful high-quality polymeric supports for the present invention include opaque white polyesters and extrusion blends of polyethylene terephthalate and polypropylene. Polyester film supports and especially poly(ethylene terephthalate) are preferred because of their excellent properties of dimensional stability. When such a polyester is used as the support material, a subbing layer may be employed to improve the bonding of the ink-receiving layer to the support. Useful subbing layers for this purpose are well known in the photographic art and include, for example, polymers of vinylidene chloride such as vinylidene chloride/acrylonitrile/acrylic acid terpolymers or vinylidene chloride/methyl acrylate/itaconic acid terpolymers.

Ink-Receiving Layer and Optional Auxiliary Layers

The ink-receiving layer contains, apart from a binder, a light-stabilizer according to formula (I) as disclosed above. The light-stabilizers are preferably added to the coating solution of the ink-receiving layer as aqueous solutions. The amount of the light-stabilizer in the receiving layer is preferably comprised between 0.5 and 3 g/m$^2$. A mixture of two or more light-stabilizers may be used. Mixtures of two or more binders can also be used in the receiving layer.

The ink-receiving layer may consist of just one single layer, or alternatively it may be composed of two layers or even of multiple layers. A particular type of an extra top ink-receiving layer may be designated as a so-called "gloss improving layer", meaning a layer which achieves a gloss of more than 30 at a 60° angle. This gloss property can be achieved by the use of swellable polymers and/or (in)organic pigments with a particle size smaller than 500 nm.

In the case of double or multiple ink-receiving layers the light-stabilizer may be incorporated in just one layer, or in several layers or in all layers. It may also be present in additional auxiliary layers, if present, such as an anti-curl backing layer.

The ink-receiving layer or in at least one of the ink-receiving layers, in the case of multiple layers, according to the present invention, may further contain a pigment.

The ink-receiving layer or in at least one of the ink-receiving layers, in the case of multiple layers, according to the present invention, may also further contain a cationic substance acting as mordant.

The ink-receiving layer, and an optional auxiliary layer, such as a backing layer for anti-curl purposes, may further contain well-known conventional ingredients, such as surfactants serving as coating aids, hardening agents, plasticizers, whitening agents and matting agents.

The ink-receiving layer and the optional auxiliary layer(s) may also be crosslinked to provide such desired features as waterfastness and non-blocking characteristics. The crosslinking is also useful in providing abrasion resistance and resistance to the formation of fingerprints on the element as a result of handling.

The different layers can be coated onto the support by any conventional coating technique, such as dip coating, knife coating, extrusion coating, spin coating, slide hopper coating and curtain coating.

Binder

The binder can be chosen from a list of compounds well-known in the art including hydroxyethyl cellulose; hydroxypropyl cellulose; hydroxyethylmethyl cellulose; hydroxypropyl methyl cellulose; hydroxybutylmethyl cellulose; methyl cellulose; sodium carboxymethyl cellulose; sodium carboxymethylhydroxethyl cellulose; water soluble ethylhydroxyethyl cellulose; cellulose sulfate; polyvinyl alcohol; vinylalcohol copolymers; polyvinyl acetate; polyvinyl acetal; polyvinyl pyrrolidone; polyacrylamide; acrylamide/acrylic acid copolymer; polystyrene, styrene copolymers; acrylic or methacrylic polymers; styrene/acrylic copolymers; ethylene-vinylacetate copolymer; vinylmethyl ether/maleic acid copolymer; poly(2-acrylamido-2-methyl propane sulfonic acid); poly(diethylene triamine-co-adipic acid); polyvinyl pyridine; polyvinyl imidazole; polyethylene imine epichlorohydrin modified; polyethylene imine ethoxylated; polyethylene oxide; polyurethane; melamine resins; gelatin; carrageenan; dextran; gum arabic; casein; pectin; albumin; starch; collagen derivatives; collodion and agar—agar.

A preferred binder for the practice of the present invention is a polyvinylalcohol (PVA), a vinylalcohol copolymer or modified polyvinyl alcohol. Most preferably, the polyvinyl alcohol is a cationic type polyvinyl alcohol, such as the cationic polyvinyl alcohol grades from Kuraray, such as POVAL C506, POVAL C118, and from Nippon Goshei.

Compound Represented by Formula (I)

According to a preferred embodiment of the ink-recording material, according to the present invention, R is selected from the group consisting of optionally substituted polyhydroxy tetrahydro-pyrans, optionally substituted polyhydroxy tetrahydrofurans, polyhydroxy straight chain alkyl groups, polyhydroxy branched alkyl groups, polyhydroxy alkyl groups substituted with optionally substituted tetrahydropyran groups and polyhydroxy alkyl groups substituted with optionally substituted tetrahydrofuran groups, wherein the carbon atoms in the chain may be substituted with an oxygen atom, a sulfur atom or a —$NR^6$— group, where $R^6$ is an alkyl group.

According to a preferred embodiment of the ink-recording material, according to the present invention, L is selected from the group consisting of a =N—$NR^7$—C(=O)—, —C(=O)—$NR^7$—$NR^8$—C(=O)—, =N—O—, =$NR^7$—$NR^8$—, —$NR^7$—$NR^8$—C(=O)—, —(C=O)$NR^7$—, —$NR^7$—O—, =N—N=, —C(=O)—$NR^7$—O— and =N—O—C(=O)— groups, wherein $R^7$ and $R^8$ independently represent a hydrogen atom or an alkyl group.

According to a particularly preferred embodiment of the ink-recording material, according to the present invention, L is selected from the group consisting of =N—NH—, —C(=O)—NH—NH—C(=O)—, =N—O—, =N—NH—C(=O)—, —NH—NH—C(=O)—, —C(=O)—NH—O—, —NH—O—, =N—$NCH_3$—C(=O)—, —C(=O)—NH—NH—, =N—N= and =N—O—C(=O)—NH— groups.

According to a preferred embodiment of the ink-recording material, according to the present invention, X is selected from the group consisting of a hydrogen atom, a —O⁻, —$OSO_2CH_3$, —C(=O)—$CH_3$, —OC(=O)—$CH_3$ and methoxy groups.

According to a preferred embodiment of the ink-recording material, according to the present invention, $R^1$, $R^2$, $R^3$ and $R^4$ are independently methyl or ethyl groups.

According to a preferred embodiment of the ink-recording material, according to the present invention, Z is selected from the group consisting of optionally substituted —$CH_2$—C(=)—$CH_2$—, —$CH_2$—CH(—)—$CH_2$—, —CH=C(—)—, —CH—C(=)— and —CH—CH(—)— groups.

According to a preferred embodiment of the compound represented by formula (I), according to the present invention, the ring is a six-membered ring to which L is covalently bonded by a single or a double bond; formula (I) of the light-stabilizer then becomes formula (II):

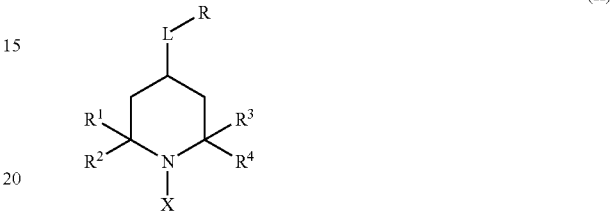

(II)

According to a further preferred embodiment of the compound represented by formula (I), according to the present invention, the ring is a five-membered ring with a double bond to which L is covalently bonded by a single bond; formula (I) of the light-stabilizer then becomes formula (III):

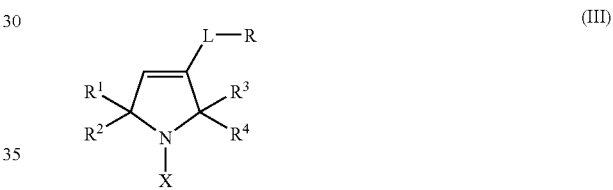

(III)

According to a further preferred embodiment of the compound represented by formula (I), according to the present invention, the ring is a five-membered ring to which L is covalently bonded by a single or a double bond; formula (I) of the light-stabilizer then becomes formula (IV):

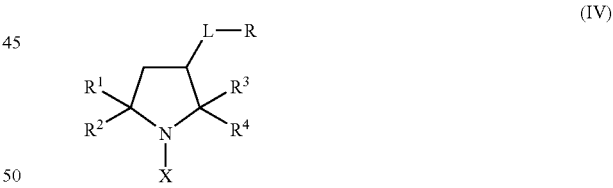

(IV)

According to a particularly preferred embodiment of the compound represented by formula (I), according to the present invention, L is a hydrazone or oxime moiety, giving rise to formula (V):

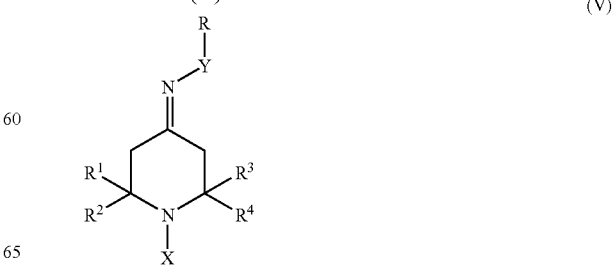

(V)

wherein Y represents an oxygen atom or $NR^5$ group; $R^5$ is selected from the group consisting of a hydrogen, a substituted or unsubstituted, saturated or unsaturated aliphatic group, a substituted or unsubstituted aromatic group, a substituted or unsubstituted hetero-aromatic group, and an acyl group.

Useful light-stabilizers include:

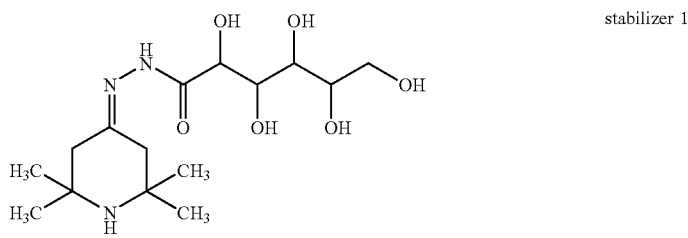

stabilizer 1

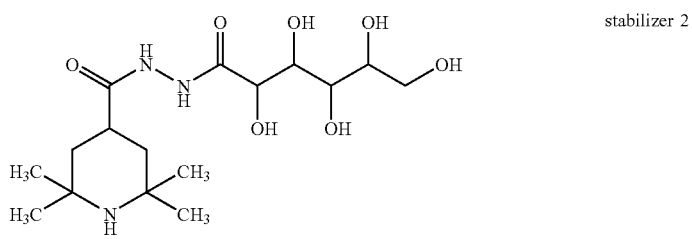

stabilizer 2

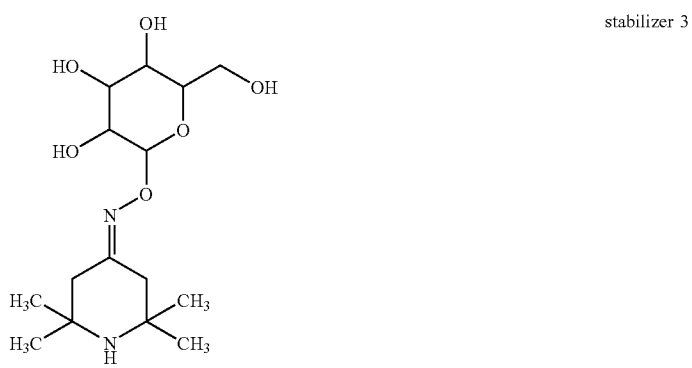

stabilizer 3

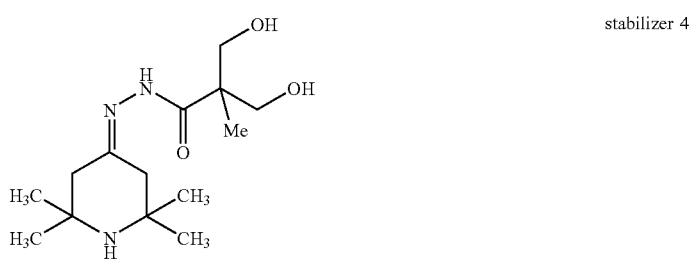

stabilizer 4

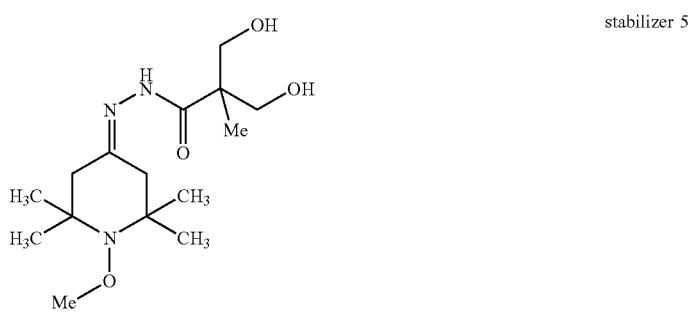

stabilizer 5

-continued
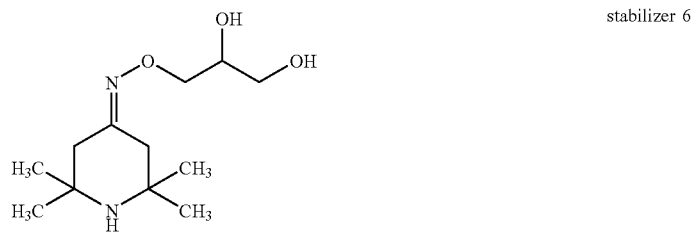
stabilizer 6
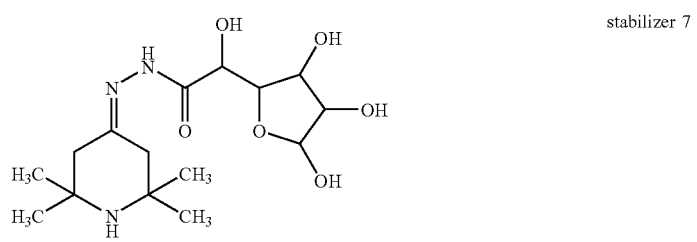
stabilizer 7
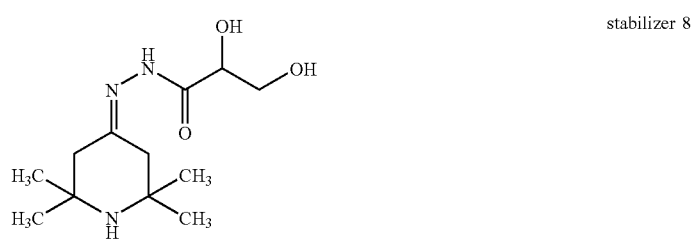
stabilizer 8
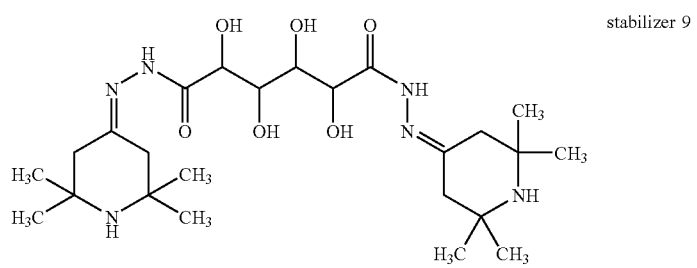
stabilizer 9
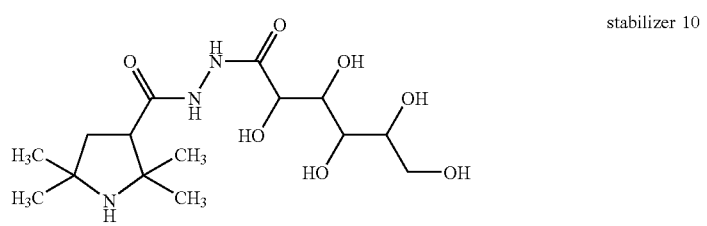
stabilizer 10
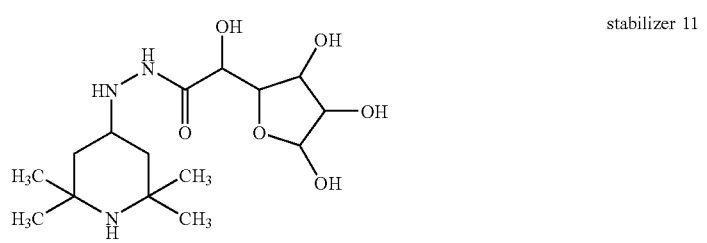
stabilizer 11

-continued
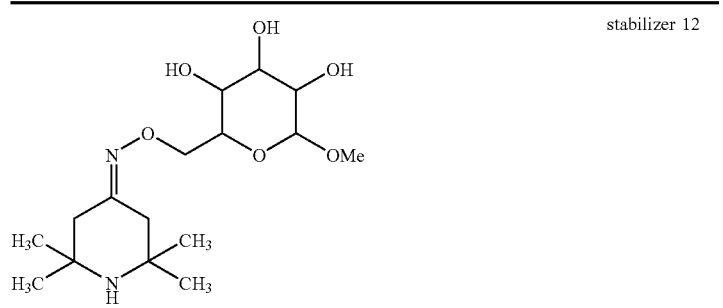 stabilizer 12
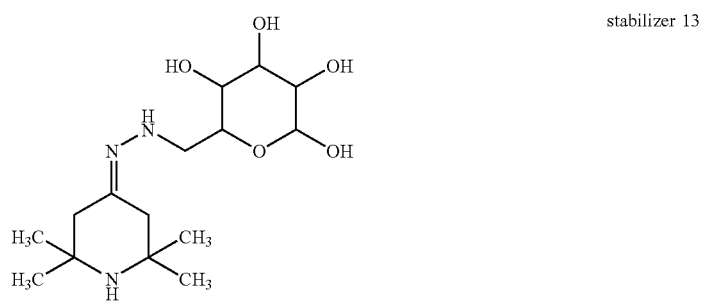 stabilizer 13
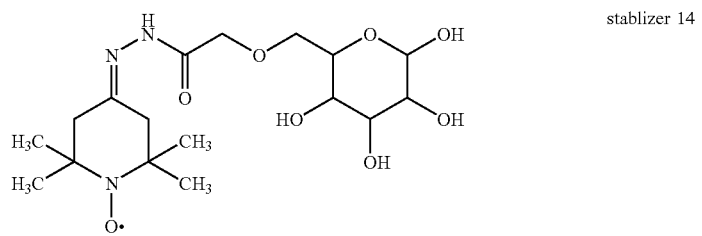 stablizer 14
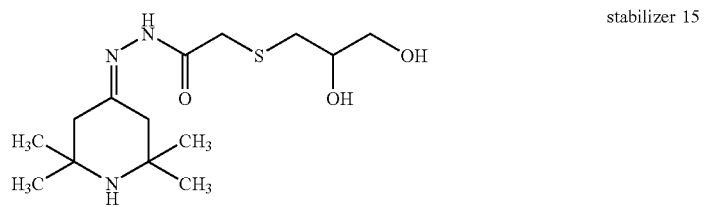 stabilizer 15
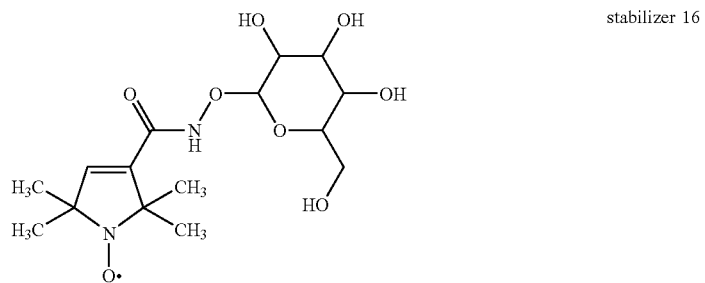 stabilizer 16
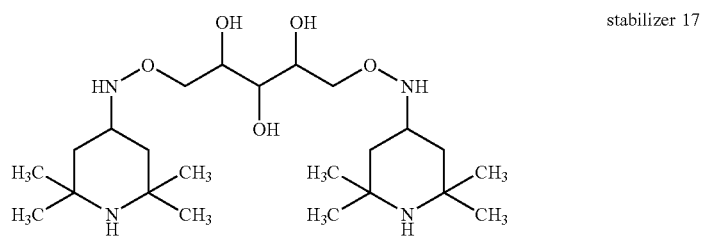 stabilizer 17

-continued
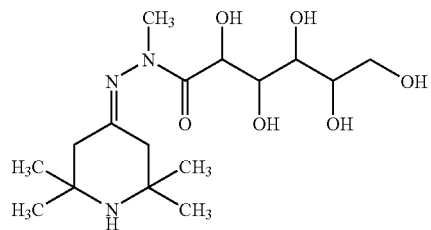
stabilizer 18
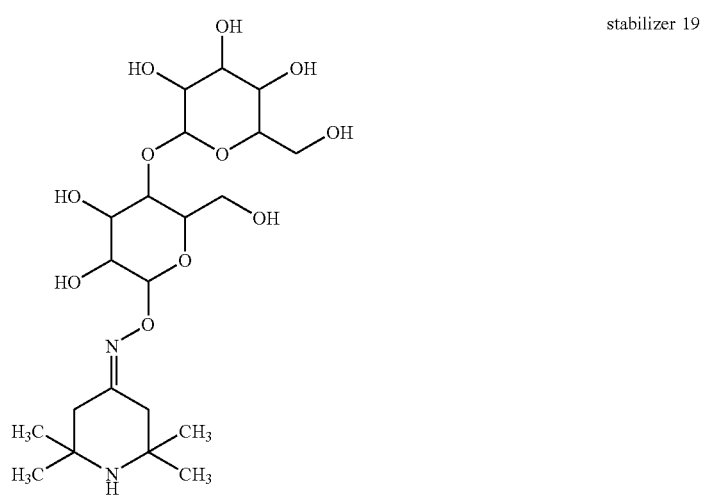
stabilizer 19
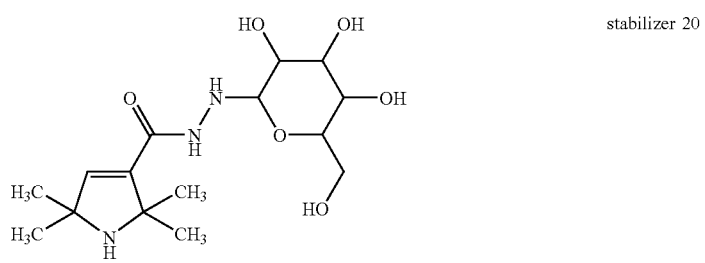
stabilizer 20
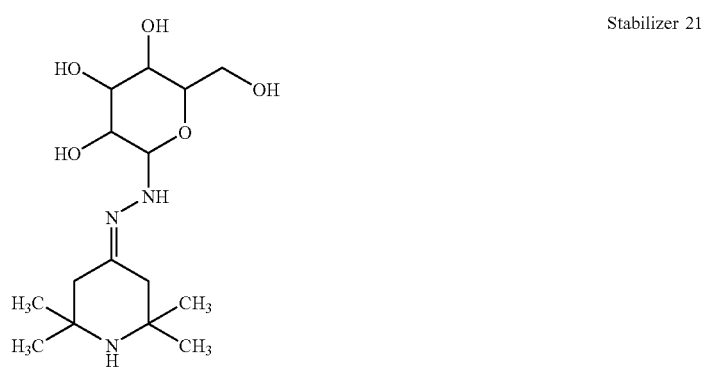
Stabilizer 21

-continued
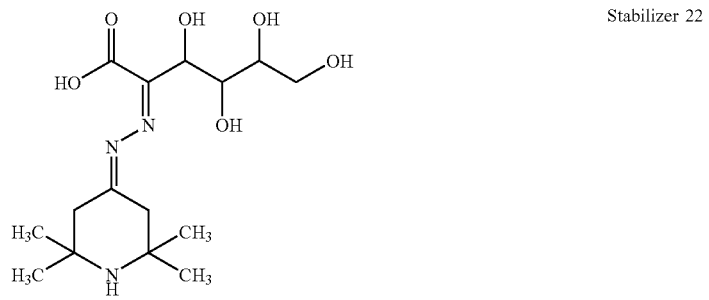
Stabilizer 22
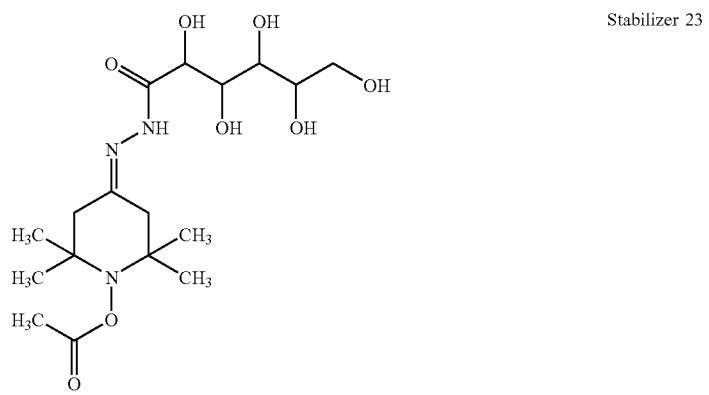
Stabilizer 23
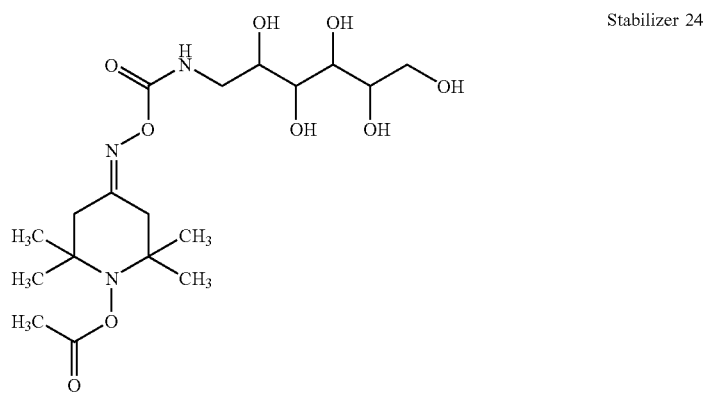
Stabilizer 24
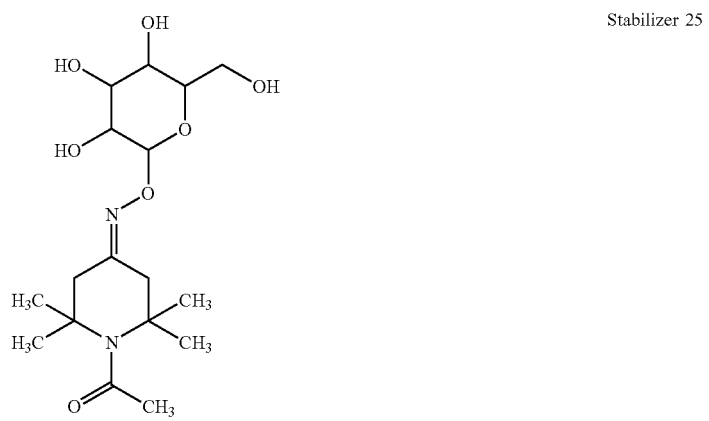
Stabilizer 25

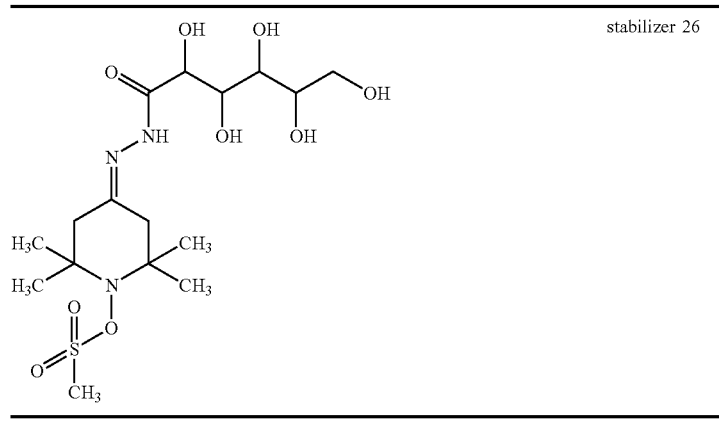

stabilizer 26

A particularly preferred compound is stabilizer 1.

All light-stabilizing compounds according to the present invention can be prepared according to well known synthetic procedures, as illustrated by some synthetic schemes for the preparation of preferred compounds. The synthetic strategies are illustrated with a few general schemes, followed by a detailed description of the synthesis of preferred compounds.

HALS-hydrazones and HALS-hydrazides can be prepared according to general scheme 1.

Scheme 1:

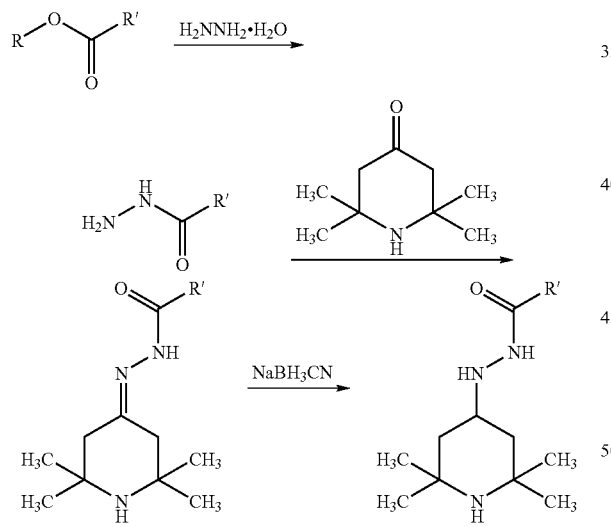

wherein R' represents a non aromatic moiety comprising at least two hydroxyl groups.

Hydrazinolysis of commercially available saccharide-lactones, such as gluconolactone, ribonic lactone and pantolactone, or esters of hydroxy-carboxylic acids yields the required intermediate hydrazides. These intermediate hydrazides smoothly react with 2,2,6,6-tetramethyl-4-piperidone, yielding oligohydroxy substituted HALS-compounds, according to the present invention. Hydrazones can be readily reduced to hydrazides, using conventional reductants, such as NaBH$_3$CN (Calabretta et al., Synthesis, 1991, 536–539), Et$_3$SiH (Wu et al., Synthesis, 1995, 435–438), NaBH$_4$ (J. Org. Chem., 1972, 37, 3615) and catalytic hydrogenation (J. Am. Chem. Soc., 1992, 114, 6266).

Using the same intermediate hydrazides, oligo-hydroxy-HALS-compounds, having a diacyl hydrazide linking group, can be prepared as illustrated in scheme 2.

Scheme 2:

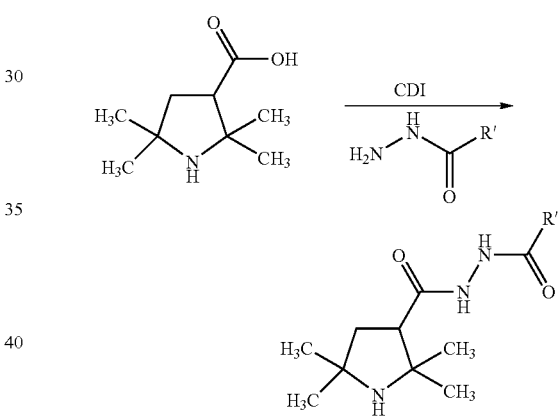

O-alkylated HALS-oximes according to the present invention can be prepared according to scheme 3.

Scheme 3:

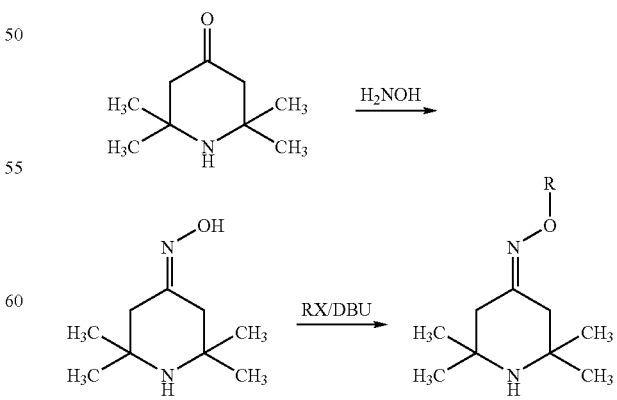

where R represents a non aromatic moiety comprising at least two hydroxyl groups.

The intermediate oxime is readily prepared by reacting hydroxylamine with 2,2,6,6-tetramethyl-4-piperidone, followed by alkylation, using 1,8-diazobicyclo[5.4.0.]undec-7-ene (DBU) or sodium methanolate as base. Intermediate protection of the alcohols and deprotection in the last synthetic step can be used if required. The HALS-oximes can be further reduced to hydroxylamines by conventional reductants.

Synthesis of stabilizer 1:

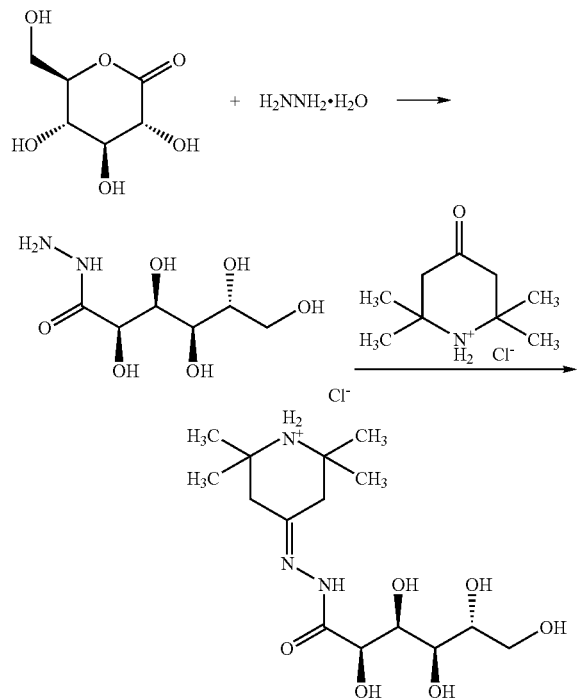

44.5 g (0.25 mol) of gluconolactone was suspended in 375 ml of ethanol. A solution of 18.75 g (0.375 mol) hydrazine hydrate in 125 ml ethanol was added to this suspension. The reaction mixture was refluxed for 6 hours. After cooling down to room temperature, the precipitated product was isolated by filtration. The crude hydrazide was redissolved in 50 ml of water and precipitated with 400 ml of methanol. The precipitated hydrazide was isolated by filtration, washed with 100 ml of methanol/water 10/1 and dried under reduced pressure. 40 g (76%) of the hydrazide was isolated (m.p.: 147–148° C.).

8.4 g (40 mmol) of the intermediate hydrazide and 7.6 g (40 mmol) of 2,2,6,6-tetramethyl-4-piperidone chlorohydrate were dissolved in 100 ml of water. The reaction was allowed to continue for 2 hours at room temperature. After 2 hours, water was evaporated under reduced pressure. The residue was treated with toluene and evaporated again. After treatment with ethanol and evaporation, 11 g (79%) of the HALS-hydrazone was isolated as a chlorohydrate.

Pigments

The pigment used is preferably an inorganic pigment, which can be chosen from neutral, anionic and cationic pigment types. Useful pigments include e.g. silica, talc, clay, hydrotalcite, kaolin, diatomaceous earth, calcium carbonate, magnesium carbonate, basic magnesium carbonate, aluminosilicate, aluminum trihydroxide, aluminum oxide (alumina), titanium oxide, zinc oxide, barium sulfate, calcium sulfate, zinc sulfide, satin white, alumina hydrate such as boehmite, zirconium oxide or mixed oxides. Preferably, the pigment is a cationic type pigment selected from alumina hydrates, aluminum oxides, aluminum hydroxides, aluminum silicates, and cationically modified silicas.

A preferred type of alumina hydrate is crystalline boehmite, or γ-AlO(OH). Useful types of boehmite include, in powder form, DISPERAL, DISPERAL HP14 and DISPERAL 40 from Sasol, MARTOXIN VPP2000-2 and GL-3 from Martinswerk GmbH.; liquid boehmite alumina systems, e.g. DISPAL 23N4-20, DISPAL 14N-25, DISPERAL AL25 from Sasol. Patents on alumina hydrate include EP 500021, EP 634286, U.S. Pat. No. 5,624,428, EP 742108, U.S. Pat. No. 6,238,047, EP 622244, EP 810101, etc. Useful cationic aluminum oxide (alumina) types include $\alpha$-$Al_2O_3$ types, such as NORTON E700, available from Saint-Gobain Ceramics & Plastics, Inc, and γ-$Al_2O_3$ types, such as ALUMINUM OXID C from Degussa; other aluminum oxide grades, such as BAIKALOX CR15 and CR30 from Baikowski Chemie; DURALOX grades and MEDIALOX grades from Baikowski Chemie, BAIKALOX CR80, CR140, CR125, B105CR from Baikowski Chemie; CAB-O-SPERSE PG003 trademark from Cabot, CATALOX GRADES and CATAPAL GRADES from from Sasol, such as PLURALOX HP14/150; colloidal $Al_2O_3$ types, such as ALUMINASOL 100; ALUMINASOL 200, ALUMINASOL 220, ALUMINASOL 300, and ALUMINASOL 520 trademarks from Nissan Chemical Industries or NALCO 8676 trademark from ONDEO Nalco.

Other useful cationic inorganic pigments include aluminum trihydroxides such as Bayerite, or $\alpha$-$Al(OH)_3$, such as PLURAL BT, available from Sasol, and Gibbsite, or γ-$Al(OH)_3$, such as MARTINAL grades from Martinswerk GmbH, MARTIFIN grades, such as MARTIFIN OL104, MARTIFIN OL 107 and MARTIFIN OL111 from Martinswerk GmbH MICRAL grades, such as MICRAL 1440, MICRAL 1500; MICRAL 632; MICRAL 855; MICRAL 916; MICRAL 932; MICRAL 932CM; MICRAL 9400 from JM Huber company; HIGILITE grades, e.g. HIGILITE H42 or HIGILITE H43M from Showa Denka K.K.

Another useful type of cationic pigment is zirconium oxide such as NALCO OOSS008 trademark of ONDEO Nalco, acetate stabilized $ZrO_2$, ZR20/20, ZR50/20, ZR100/20 and ZRYS4 trademarks from Nyacol Nano Technologies.

Useful mixed oxides are SIRAL grades from Sasol, colloidal metal oxides from Nalco such as Nalco 1056, Nalco TX10496, Nalco TX11678.

Another preferred type of inorganic pigment is silica which can be used as such in its anionic form or after cationic modification. Silica as pigment in ink receiving elements is disclosed in numerous old and recent patents, e.g. U.S. Pat. No. 4,892,591, U.S. Pat. No. 4,902,568, EP 373573, EP 423829, EP 487350, EP 493100, EP 514633, etc. The silica can be chosen from different types, such as crystalline silica, amorphous silica, precipitated silica, fumed silica, silica gel, spherical and non-spherical silica. The silica may contain minor amounts of metal oxides from the group Al, Zr, Ti. Useful types include AEROSIL OX50 (BET surface area 50±15 $m^2/g$, average primary particle size 40 nm, $SiO_2$ content>99.8%, $Al_2O_3$ content<0.08%), AEROSIL MOX170 (BET surface area 170 g/$m^2$, average primary particle size 15 nm, $SiO_2$ content>98.3%, $Al_2O_3$ content 0.3–1.3%), AEROSIL MOX80 (BET surface area 80±20 g/$m^2$, average primary particle size 30 nm, $SiO_2$ content>98.3%, $Al_2O_3$ content 0.3–1.3%), or other hydrophilic AEROSIL grades available from Degussa-Hüls AG, which may give aqueous dispersions with a small average particle size (<500 nm).

Cationically modified silica can be prepared by following methods, without meaning to be limitative:
(1) subjecting silica to a surface treatment with an inorganic cationic compound such as particular metal oxides and oxyhydroxides, e.g. aluminum oxides, and alumina hydrates such as boehmite and pseudo-boehmite; a useful cationic inorganic compound to modify silica is pseudo-boehmite. Pseudo-boehmite is also called boehmite gel and is fine particulate alumina hydrate having a needle form. The composition thereof is generally represented by $Al_2O_3.1.5-2H_2O$ and differs from that of crystalline boehmite;
(2) by subjecting silica to a surface treatment with an organic compound having both an amino group or quaternary ammonium group thereof or a quaternary phosphonium group, and a functional group having reactivity to a silanol group on the surface of silica, such as aminoalkoxysilane or aminoalkyl glycidyl ether or isopropanol amine;
(3) by polymerisation of a cationic or amino functional monomer in the presence of a silica.

In an alternative embodiment the pigment may be chosen from organic particles such as polystyrene, polymethyl methacrylate, silicones, melamine-formaldehyde condensation polymers, ureaformaldehyde condensation polymers, polyesters and polyamides. Mixtures of inorganic and organic pigments can be used. However, most preferably the pigment is an inorganic pigment.

Mixtures of two or more piments may be used.

For obtaining glossy ink-receiving layers the particle size of the pigment should preferably be smaller than 500 nm. In order to obtain a porous glossy layer which can serve as an ink-receiving layer for fast ink uptake the pigment/binder ratio should be at least 4. Only at these high ratios the binder is no longer able to fill up all pores and voids created by the pigments in the coating. To achieve a sufficient porosity of the coating for fast ink uptake the pore volume of these highly pigmented coatings should be higher than 0.1 ml/g of coated solids. This pore volume can be measured by gas adsorption (nitrogen) or by mercury diffusion.

Cationic Substance Acting as a Mordant

Cationic substances acting as a mordant increase the capacity of the layer for fixing and holding the dye of the ink droplets. A particularly suited compound is a poly(diallyldimethylammonium chloride) or, in short, a poly(DADMAC). These compounds are commercially available from several companies, e.g. Aldrich, Nalco, CIBA, Nitto Boseki Co., Clariant, BASF and EKA Chemicals. Other useful cationic compounds include DADMAC copolymers such as copolymers with acrylamide, e.g NALCO 1470 trade mark of ONDEO Nalco or PAS-J-81, trademark of Nitto Boseki Co., such as copolymers of DADMAC with acrylates, such as Nalco 8190, trademark of ONDEO Nalco; copolymers of DADMAC with $SO_2$, such as PAS-A-1 or PAS-92, trademarks of Nitto Boseki Co., copolymer of DADMAC with maleic acid, e.g. PAS-410, trademark of Nitto Boseki Co., copolymer of DADMAC with diallyl(3-chloro-2-hydroxypropyl)amine hydrochloride, eg. PAS-880, trademark of Nitto Boseki Co., dimethylamine-epichlorohydrine copolymers, e.g. Nalco 7135, trademark of ONDEO Nalco or POLYFIX 700, trade name of Showa High Polymer Co.; other POLYFIX grades which could be used are POLYFIX 601, POLYFIX 301, POLYFIX 301A, POLYFIX 250WS, and POLYFIX 3000; NEOFIX E-117, trade name of Nicca Chemical Co., a polyoxyalkylene polyamine dicyanodiamine, and REDIFLOC 4150, trade name of EKA Chemicals, a polyamine; MADAME (methacrylatedimethylaminoethyl=dimethylaminoethyl methacrylate) or MADQUAT (methacryloxyethyltrimethylammonium chloride) modified polymers, e.g. ROHAGIT KL280, ROHAGIT 210, ROHAGIT SL144, PLEX 4739L, PLEX 3073 from Röhm, DIAFLOC KP155 and other DIAFLOC products from Diafloc Co., and BMB 1305 and other BMB products from EKA chemicals; cationic epichlorohydrin adducts such as POLYCUP 171 and POLYCUP 172, trade names from Hercules Co.; from Cytec industries: CYPRO products, e.g. CYPRO 514/515/516, SUPERFLOC 507/521/567; cationic acrylic polymers, such as ALCOSTAT 567, trademark of CIBA, cationic cellulose derivatives such as CELQUAT L-2OO, H-1OO, SC-240C, SC-230M, trade names of Starch & Chemical Co., and QUATRISOFT LM200, UCARE polymers JR125, JR400, LR400, JR30M, LR30M and UCARE polymer LK; fixing agents from Chukyo Europe: PALSET JK-512, PALSET JK512L, PALSET JK-182, PALSET JK220, WSC-173, WSC-173L, PALSET JK-320, PALSET JK-320L and PALSET JK-350; polyethyleneimine and copolymers, e.g. LUPASOL, trade name of BASF AG; triethanolamine-titanium-chelate, e.g. TYZOR, trade name of Du Pont Co.; copolymers of vinylpyrrolidone such as VIVIPRINT 111, trade name of ISP, a methacrylamido propyl dimethylamine copolymer; with dimethylaminoethylmethacrylate such as COPOLYMER 845 and COPOLYMER 937, trade names of ISP; with vinylimidazole, e.g. LUVIQUAT CARE, LUVITEC 73W, LUVITEC VPI55 K18P, LUVITEC VP155 K72W, LUVIQUAT FC905, LUVIQUAT FC550, LUVIQUAT HM522, and SOKALAN HP56, all trade names of BASF AG; polyamidoamines, e.g. RETAMINOL and NADAVIN, trade marks of Bayer AG; phosphonium compounds such as disclosed in EP 609930 and other cationic polymers such as NEOFIX RD-5, trademark of Nicca Chemical Co.

Surfactants

Surfactants may be incorporated in the layers of the recording element of the present invention. They can be any of the cationic, anionic, amphoteric, and non-ionic ones as described in JP-A 62-280068 (1987). Examples of the surfactants are N-alkylamino acid salts, alkylether carboxylic acid salts, acylated peptides, alkylsulfonic acid salts, alkylbenzene and alkylnaphthalene sulfonic acid salts, sulfosuccinic acid salts, α-olefin sulfonic acid salts, N-acylsulfonic acid salts, sulfonated oils, alkylsulfonic acid salts, alkylether sulfonic acid salts, alkylallylethersulfonic acid salts, alkylamidesulfonic acid salts, alkylphosphoric acid salts, alkyletherphosphoric acid salts, alkylallyletherphosphoric acid salts, alkyl and alkylallylpolyoxyethylene ethers, alkylallylform-aldehyde condensed acid salts, alkylallylethersulfonic acid salts, alkylamidesulfonic acid salts, alkylphosphoric acid salts, alkyletherphosphoric acid salts, alkylallyletherphosphoric acid salts, alkyl and alkylallylpolyoxyethylene ethers, alkylallylformaldehyde condensed polyoxyethylene ethers, blocked polymers having polyoxypropylene, polyoxyethylene polyoxypropylalkylethers, polyoxyethyleneether of glycolesters, polyoxyethylene-ether of sorbitanesters, polyoxyethyleneether of sorbitolesters, polyethyleneglycol aliphatic acid esters, glycerol esters, sorbitane esters, propyleneglycol esters, sugaresters, fluoro $C_2-C_{10}$ alkyl-carboxylic acids, disodium N-perfluorooctanesulfonyl glutamate, sodium 3-(fluoro-$C_6$–$C_{11}$-alkyloxy)-1-$C_3$–$C_4$ alkyl sulfonates, sodium 3-($\omega$-fluoro-$C_6$-$C_8$alkanoyl-N-ethylamino)-1-propane sulfonates, N-[3-(perfluorooctanesulfonamide)-propyl]-N,N-dimethyl-N-carboxymethylene ammonium betaine, fluoro-C11–$C_{20}$ alkylcarboxylic acids, perfluoro-$C_7$–$C_{13}$-alkyl-carboxylic acids, perfluorooctane sulfonic acid diethanolamide, Li, K and Na perfluoro-$C_4$–$C_{12}$-alkyl sulfonates, N-propyl-N-(2-hydroxyethyl)perfluorooctane sulfonamide, perfluoro-$C_6$–$C_{10}$-alkylsulfonamide-propyl-sulfonyl-glycinates, bis-(N-perfluorooctylsulfonyl-N-ethanolaminoethyl) phosphonate, mono-perfluoro $C_6$–$C_{16}$ alkyl-ethyl phosphonates and perfluoroalkyl-betaine.

Useful cationic surfactants include N-alkyl dimethyl ammonium chloride, palmityl trimethyl ammonium chloride, dodecyldimethylamine, tetradecyldimethylamine, ethoxylated alkyl guanidine-amine complex, oleamine hydroxypropyl bistrimonium chloride, oleyl imidazoline, stearyl imidazoline, cocamine acetate, palmitamine, dihydroxyethylcocamine, cocotrimonium chloride, alkyl polyglycolether ammonium sulphate, ethoxylated oleamine, lauryl pyridinium chloride, N-oleyl-1,3-diaminopropane, stearamidopropyl dimethylamine lactate, coconut fatty amide, oleyl hydroxyethyl imidazoline, isostearyl ethylimidonium ethosulphate, lauramidopropyl PEG-dimonium-chloride phosphate, palmityl trimethylammonium chloride, and cetyltrimethylammonium bromide.

Especially useful are the fluorocarbon surfactants as described in e.g. U.S. Pat. No. 4,781,985, having a structure of: $F(CF_2)_{4-9}CH_2CH_2SCH_2CH_2N^+R_3X^-$ wherein R is a hydrogen or an alkyl group; and in U.S. Pat. No. 5,084,340, having a structure of: $CF_3(CF_2)_mCH_2CH_2O(CH_2CH_2O)_nR$ wherein m=2 to 10; n=1 to 18; R is hydrogen or an alkyl group of 1 to 10 carbon atoms. These surfactants are commercially available from DuPont and 3M. The concentration of the surfactant component in the ink-receiving layer is typically in the range of 0.1 to 2%, preferably in the range of 0.4 to 1.5% and is most preferably 0.75% by weight based on the total dry weight of the layer.

Plasticizers

The ink-receiving layer and the optional auxiliary layer(s) may also comprise a plasticizer such as ethylene glycol, diethylene glycol, propylene glycol, polyethylene glycol, glycerol monomethylether, glycerol monochlorohydrin, ethylene carbonate, propylene carbonate, urea phosphate, triphenylphosphate, glycerol-monostearate, propylene glycol monostearate, tetramethylene sulfone, n-methyl-2-pyrrolidone, n-vinyl-2-pyrrolidone.

Crosslinking Agents

There are a vast number of known crosslinking agents—also known as hardening agents—that will function to crosslink film forming binders. Hardening agents can be used individually or in combination and in free or in blocked form. A great many hardeners, useful for the present invention, are known, including formaldehyde and free dialdehydes, such as succinaldehyde and glutaraldehyde, blocked dialdehydes, active esters, sulfonate esters, active halogen compounds, isocyanate or blocked isocyanates, polyfunctional isocyanates, melamine derivatives, s-triazines and diazines, epoxides, active olefins having two or more active bonds, carbodiimides, zirconium complexes, e.g. BACOTE 20, ZIRMEL 1000 or zirconium acetate, trademarks of MEL Chemicals, titanium complexes, such as TYZOR grades from DuPont, isoxazolium salts subsituted in the 3-position, esters of 2-alkoxy-N-carboxy-dihydroquinoline, N-carbamoylpyridinium salts, hardeners of mixed function, such as halogen-substituted aldehyde acids (e.g. mucochloric and mucobromic acids), onium substituted acroleins and vinyl sulfones and polymeric hardeners, such as dialdehyde starches and copoly(acroleinmeth-acrylic acid), and oxazoline functional polymers, e.g. EPOCROS WS-500, and EPOCROS K-1000 series, and maleic anhydride copolymers, e.g. GANTREZ AN119.

In the practice of this invention boric acid is a preferred crosslinker.

The present invention will now be illustrated by the following examples without however being limited thereto.

EXAMPLE 1

Preparation of the Coating Solution:

To apply the light-stabilizing agent to ink jet print media, a coating liquid was prepared by adding 25 parts by solid weight of a 10% aqueous solution of compound Stabilizer 1 (ST1) (see list of stabilizers in the Detailed Description section) to 170 parts of water.

Coating and Evaluation of the Coated Samples:

The coating solution was applied to a glossy porous media (Agfajet Universal Instant Dry Photograde Paper Glossy) as the base coat. In order to change the concentration of the light-stabilizing additive, the thickness of the applied coating solution was varied. The application was performed by means of a doctor blade coater. The comparative samples were obtained by simply applying the aqueous solution to the recording media without the stabilizing agent.

After the media were allowed to dry at room temperature for 24 hours, color patches with 50% and 100% ink of cyan, magenta, yellow and black were printed by means of a printer HP970Cxi (trademark of Hewlett-Packard). The black patches were obtained by printing cyan, magenta and yellow. The light-fastness was evaluated by measuring the relative optical density loss of the printed samples after being exposed to light in a fade-o-meter, XENOTEST 150 (trademark: Original Hanau) with 180 kLux during 16 hours. The results are summarised in table 1.

TABLE 1 comparison of optical density loss of printed media (50% patches) treated with and without light-stabilizing additive:

| | Relative optical density loss (%) | | |
|---|---|---|---|
| Color | Without ST-1 | With 0.5 g/m² of ST-1 | with 1.5 g/m² of ST-1 |
| Yellow | 24.0 | 15.1 | 14.8 |
| Magenta | 31.0 | 14.8 | 16.1 |
| Cyan | 28.6 | 23.5 | 26.9 |
| Black | 26.8 | 10.7 | 12.5 |

As can be seen from the table, the porous material impregnated with stabilizer ST-1 shows an important improvement in light-fastness.

EXAMPLE 2

Two ink jet recording media (invention and comparative) were prepared by coating on a resin-coated paper an ink-receiving layer which composition is shown in table 2. The coating weight of the inorganic pigment was 30.0 g/m². On top of this layer, a gloss improving layer was coated containing 100 parts of the commercial boehmite DISPERAL HP 14/2, from Sasol Co., a 25% dispersion in water, 2 parts of a polyvinyl alcohol from Nippon Goshei Co., 0.2 parts of boric acid and 0.8 parts of cetyl-ammonium bromide. The coating thickness was chosen to achieve a pigment coating weight of 5 g/m². The invention sample contained 20 parts ST-1 in the top layer, the comparative sample not.

TABLE 2

| Compositions | |
|---|---|
| Alumina (Cab-o-Sperse PG003: 40%, supplied by Cabot Corp.) | 704.3 g |
| Polyvinyl alcohol (Gohsefimer K210, supplied by Nippon Gohsei) | 18.3 g |
| Pseudo-boehmite DISPERAL P3 (trade name of Sasol Co.) | 28.2 g |
| Boric acid | 1.8 g |
| Deionised water | 477.5 g |

Color patches with 50% and 100% ink of cyan, magenta, yellow and black were printed on both samples by means of a of a printer HP970Cxi (trademark of Hewlett-Packard). The light-fastness was evaluated by measuring the relative optical density loss of the printed samples after being exposed to light in a fade-o-meter, XENOTEST 150 (trademark of Original Hanau) with 180 kLux during 16 hours.

The relative loss (%) in density of the four 50% color patches together, due to the light fading are shown in table 3.

TABLE 3

| Color | Comparative sample | Invention sample |
|---|---|---|
| Yellow | 42.3 | 42.6 |
| Magenta | 80.3 | 66.1 |
| Cyan | 49.0 | 50.0 |
| Black | 54.4 | 47.5 |

As can be seen, the color stability, especially for the magenta ink and the black color (obtained from cyan, magenta and yellow ink), was much improved when compound ST-1 was introduced in the ink-receiving layer.

Having described in detail preferred embodiments of the current invention, it will now be apparent to those skilled in the art that numerous modifications can be made therein without departing from the scope of the invention as defined in the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An ink jet recording material comprising a support and at least one binder containing ink-receiving layer, characterized in that said at least one ink-receiving layer further contains a compound according to following general formula (I):

$$A\text{-}L\text{-}R \qquad (I)$$

wherein,

A is represented by following formula:

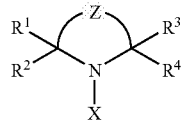

wherein:

Z represents the necessary atoms to complete a five- or six-membered ring, $R^1$ to $R^4$ independently represent a substituted or unsubstituted C1 to C6 aliphatic group, X is selected from the group consisting of a hydrogen, a substituted or unsubstituted aliphatic group, an acyl group, an oxy radical, a hydroxyl group, an alkoxy group an —OSO$_2$-alkyl group, and an acyloxy group;

L is a divalent linking group, linked to the five- or six-membered ring by one of the atoms of Z, optionally by a double bond, wherein said divalent linking group comprises a nitrogen-nitrogen or nitrogen-oxygen bond, —R represents a non aromatic moiety comprising at least two hydroxyl groups.

2. Ink-jet recording material according to claim 1, wherein said recording material further comprises a pigment in at least one ink-receiving layer.

3. Ink-jet recording material according to claim 2 wherein said pigment is an inorganic pigment.

4. Ink-jet recording material according to claim 3 wherein said inorganic pigment is chosen from the group consisting of silica, alumina, aluminum silicate, and aluminum trihydroxide.

5. An ink jet recording material comprising a support and at least one binder containing ink-receiving layer, characterized in that said at least one ink-receiving layer further contains a compound according to following general formula (II):

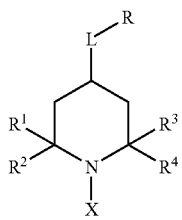

wherein,
- $R^1$ to $R^4$ independently represent a substituted or unsubstituted C1 to C6 aliphatic group,
- X is selected from the group consisting of a hydrogen, a substituted or unsubstituted aliphatic group, an acyl group, an oxy radical, a hydroxyl group, an alkoxy group an —$OSO_2$-alkyl group, and an acyloxy group,
- L is a divalent linking group, linked to the six-membered ring optionally by a double bond, wherein said divalent linking group comprises a nitrogen-nitrogen or nitrogen-oxygen bond,
- R represents a non aromatic moiety comprising at least two hydroxyl groups.

6. An ink jet recording material according to claim 5, wherein said compound is represented by following formula (V):

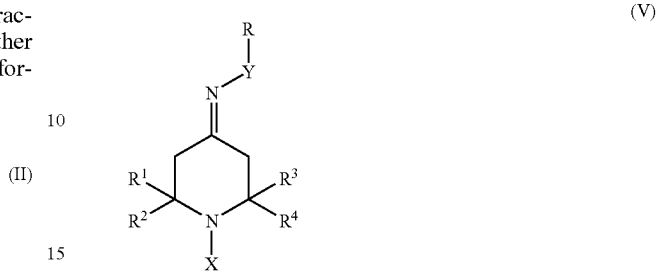

wherein,
- $R^1$ to $R^4$ independently represent a substituted or unsubstituted C1 to C6 aliphatic group,
- X is selected from the group consisting of a hydrogen, a substituted or unsubstituted aliphatic group, an acyl group, an oxy radical, a hydroxyl group, an alkoxy group an —$OSO_2$-alkyl group, and an acyloxy group,
- Y represents an oxygen or $NR^5$; $R^5$ is selected from the group consisting of a hydrogen, a substituted or unsubstituted, saturated or unsaturated aliphatic group, a substituted or unsubstituted aromatic group, a substituted or unsubstituted hetero-aromatic group, and an acyl group; and
- R represents a non-aromatic moiety comprising at least two hydroxyl groups.

7. Ink-jet recording material according to any of claims 1 to 4 wherein said binder is a polyvinyl alcohol.

* * * * *